United States Patent [19]
Harroff

[11] 3,935,858
[45] Feb. 3, 1976

[54] KNEE IMMOBILIZER
[75] Inventor: Marlin R. Harroff, Bourbon, Ind.
[73] Assignee: Orthopedic Equipment Company, Inc., Bourbon, Ind.
[22] Filed: Jan. 13, 1975
[21] Appl. No.: 540,505

[52] U.S. Cl. ............................... 128/80 C; 128/165
[51] Int. Cl.² .......................................... A61F 3/00
[58] Field of Search... 128/133, 80 C, 165, DIG. 15, 128/87 R, 80 R

[56]  References Cited
UNITED STATES PATENTS
3,587,572  6/1971  Evans................................ 128/80 C
3,831,467  8/1974  Moore............................... 128/80 C OTHER PUBLICATIONS
Richards Orthopedic & Otological Instruments Catalogue of 1966, p. 17.

Primary Examiner—Lawrence W. Trapp
Attorney, Agent, or Firm—Oltsch & Knoblock

[57]  ABSTRACT

A wraparound immobilizer for the knee in which the inside and outside stays which assist in immobilizing the knee are adjustable to accommodate the size of the patient. Additionally, the stays may carry the attachment straps by which the immobilizer is secured about the knee.

5 Claims, 6 Drawing Figures

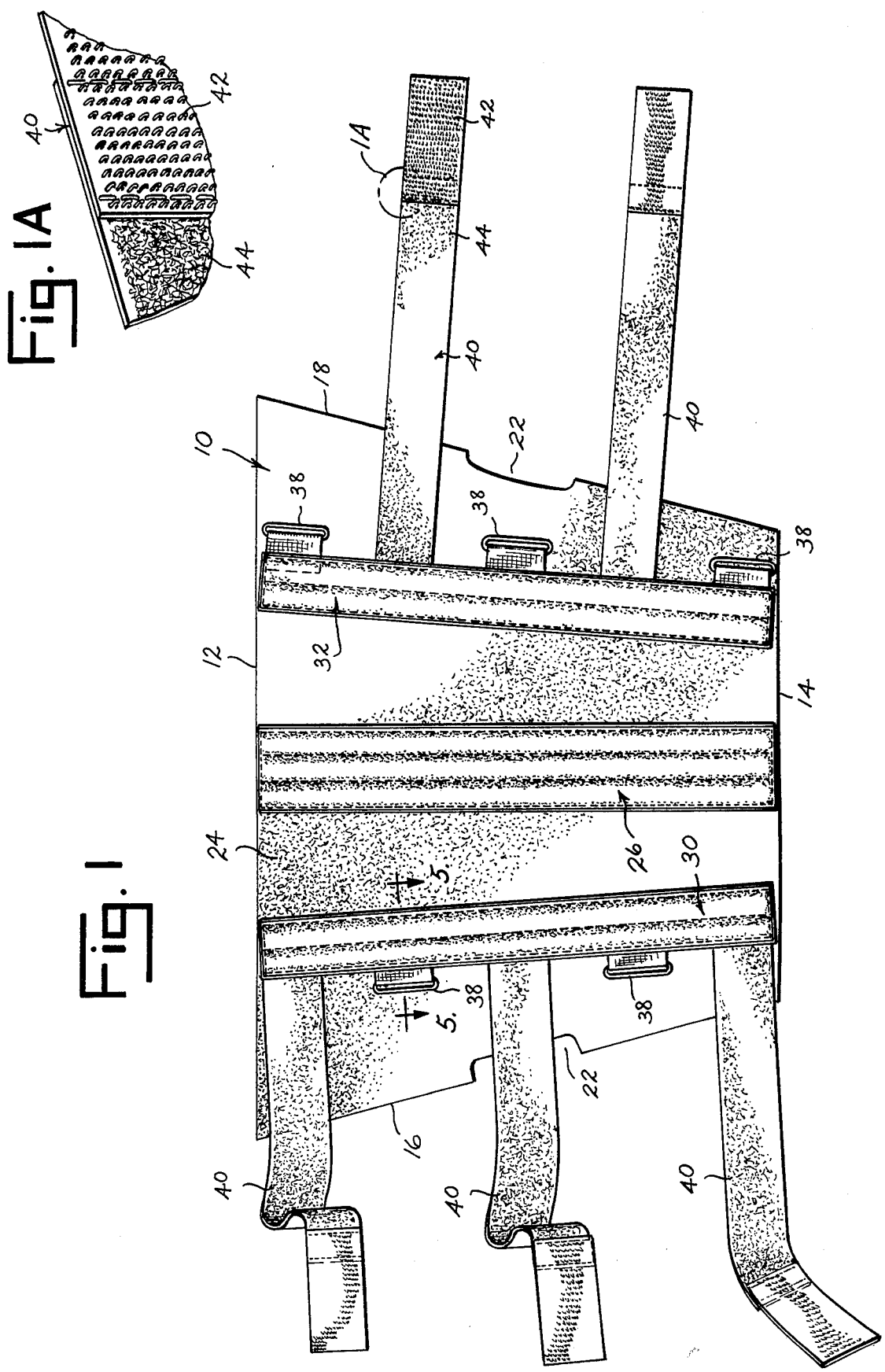

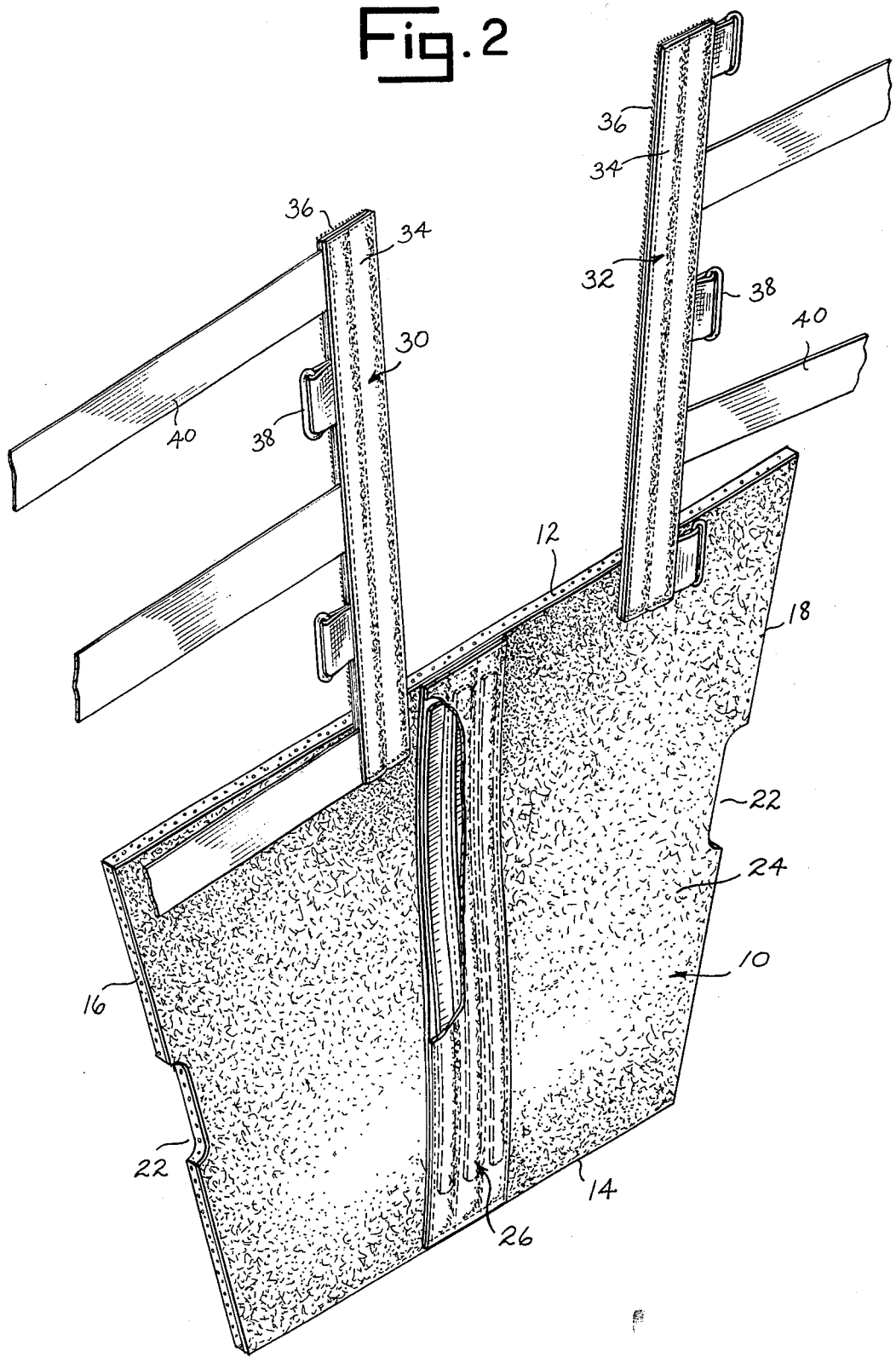

U.S. Patent   February 3, 1976   Sheet 3 of 3   3,935,858
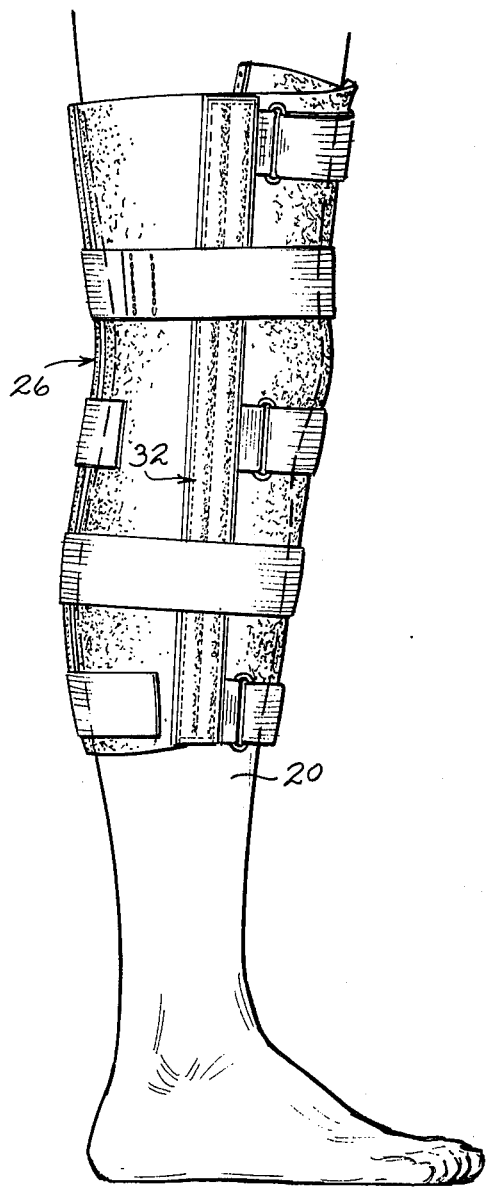
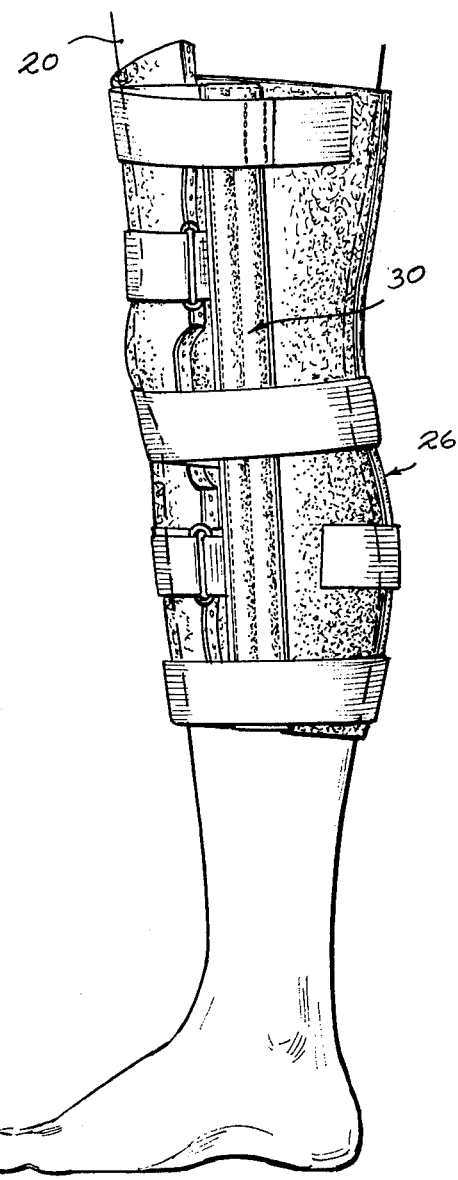
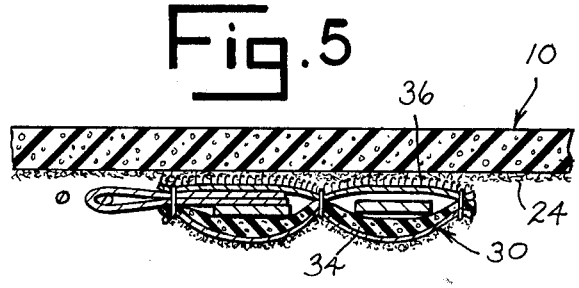

KNEE IMMOBILIZER

SUMMARY OF THE INVENTION

This invention relates to an orthopedic device for immobilizing the knee and will have specific application to a knee immobilizer which is of universal application to accommodate patients of varying size.

The immobilizer includes a flexible cover which extends around the knee of the patient. A pair of stays are detachably connected to the cover and positioned one on the inside and one on the outside of the knee. The stays may also carry belts or similar securement means by which the cover of the immobilizer is secured about the patient's leg. The position of the pair of stays by being detachably connected to the immobilizer cover can be varied so as to accommodate the particular size of the patient.

Accordingly, it is an object of this invention to provide an immobilizer for the knee which is of universal application to accommodate patients of different size.

Another object of this invention is to provide a wrap-around immobilizer for the knee in which stays are adjustably applied to the cover of the immobilizer.

Still another object of this invention is to provide an immobilizer which is for the knee and which includes detachable stays positioned on the inside and outside of the knee and carrying means for securing the cover about the knee.

And still another object of this invention is to provide a knee immobilizer which is of universal application and which can be simply applied to the patient.

Other objects of this invention will become apparent upon a reading of the invention's description.

BRIEF DESCRIPTION OF THE DRAWINGS

A preferred embodiment of this invention has been chosen for illustration and description wherein:

FIG. 1 is a plan view of the immobilizer shown in detached form.

FIG. 1A is a detailed view of that portion of FIG. 1 within broken line circle 1A.

FIG. 2 is a plan view of the immobilizer showing the stays thereof detached from the immobilizer.

FIG. 3 is a perspective view of the immobilizer shown applied about the knee of a patient and as viewed from one side.

FIG. 4 is also a perspective view of the immobilizer shown applied about the knee of the patient and viewed from the opposite side.

FIG. 5 is a fragmentary cross sectional view taken along line 5—5 of FIG. 1.

DESCRIPTION OF THE PREFERRED EMBODIMENT

The preferred embodiment illustrated is not intended to be exhaustive or to limit the invention to the precise form disclosed. It is chosen and described in order to best explain the principles of the invention and its application and practical use to thereby enable others skilled in the art to best utilize the invention.

The immobilizer includes a flexible cover 10. Cover 10 includes an upper edge 12 and a parallel lower edge 14, as well as side edges 16 and 18. To accommodate the anatomical shape of a patient's leg 20, side edges 16 and 18 preferably taper from upper edge 12 to lower edge 14 with the cover assuming a trapezoidal appearance when in planar form. Also each side edge 16 and 18 may be formed with a cut-out 22 to accommodate the knee cap of the patient. Cover 10 may be formed of any one of a variety of materials, such as a polyvinyl foam construction, having a looped pile material 24 applied to its outer surface. A fixed stay 26 is positioned midway between side edges 16 and 18 and extends from upper edge 12 to lower edge 14 of the cover. Stay 26 is secured in position by being sewn or otherwise appropriately affixed to cover 10. Stay 26 is shaped to generally conform to the anatomical curvature of the back of the leg at the knee.

Also connected to cover 10 are a pair of detachable stays 30 and 32. Stays 30 and 32 are located to the inside and outside of the knee when the immobilizer is secured about the patient as shown in FIGS. 3 and 4. Each stay 30 and 32 includes an encasement 34 to which a plurality of hook or similar type securement members 36 are attached to one side. Hook members 36 are designed so as to engage and interlock with the loop pile material 24 of cover 10 and serve to connect stays 30 and 32 to the cover. Hook members 36 of stays 30 and 32 and loop pile material 24 of cover 10 may be of the cooperating interlocking type sold under the well known trademark "Velcro." Stays 30 and 32 are connected to cover 10 by having their hook members 36 pressed into engagement with loop pile material 24 of the cover. Rings 38 and straps 40 are also secured to stays 30 and 32 for the purpose of securing cover 10 about the knee of the patient.

In FIGS. 3 and 4 the immobilizer is shown attached to leg 20. Cover 10 is wrapped around the knee with stay 26 being positioned to the rear or back of the knee and with side edges 16 and 18 in a juxtaposed or overlapping arrangement, depending upon the size of the patient. Stays 30 and 32 are applied to the cover at selected locations on the inside and outside of the knee, thus providing lateral rigidity to the immobilizer. The free end portions of straps 40 are inserted through rings 38 and return bent so that the hook members 42 of each strap can be pressed into interlocking engagement with the pile material 44 extending along the remainder of the strap.

By utilizing loop pile material with cover 10 and hook member attachments with stays 30 and 32, the stays can be easily removed from and reapplied to the cover in adjusting the immobilizer to accommodate to a particular size patient. The interlocking adherence between hook members 36 of stays 30 and 32 and the loop pile material of cover 10 is of sufficient strength to enable the cover to be secured about the patient's knee through the use of rings 38 and straps 40.

While it is preferred that stays 30 and 32 of the immobilizer also carry the means for securing cover 10 about the knee of the patient, it is to be understood that such securement means whether straps, rings or buckles can be sewn directly to cover 10 with detachable stays 30 and 32 serving only as rigidifying means. Further, it is to be understood that the invention is not to be limited to the details above given but may be modified within the scope of the appended claims.

What I claim is:

1. An immobilizer for the knee of a patient comprising a flexible cover means having in planar orientation upper and lower edges and opposite side edges, a first rigidifying means connected to said cover means between said side edges and extending from adjacent the upper edge to adjacent the lower edge of the cover means, said first rigidifying means for positioning behind the knee when said cover means is applied to the patient, second and third rigidifying means, each second and third rigidifying means including means for detachable and adjustable securement to said cover means, and means for securing said cover means about said knee, said second rigidifying means being adjustably secured to said cover means between said first rigidifying means and one cover means side edge for positioning at the inside of said knee when said cover means is applied to the patient, said third rigidifying means being adjustably secured to said cover means between said first rigidifying means and the other cover means side edge for positioning at the outside of said knee when the cover means is applied to the patient, said securing means for the cover means being carried by said second and third rigidifying means.

2. The knee immobilizer of claim 1 wherein said securing means includes a strap member with one end affixed to said second rigidying means, a part of said securing means carried by said third rigidifying means for interlocking with said strap member to secure said cover means about said knee.

3. The knee immobilizer of claim 2 wherein said interlocking means of said third rigidifying means is a ring means for accommodating the opposite end of said strap member.

4. An immobilizer for the knee of a patient comprising a flexible cover means having in planar orientation upper and lower edges and opposite side edges, said cover means including an outer surface formed of loop means, a first rigidifying means connected to said cover means between said side edges and extending from adjacent the upper edge to adjacent the lower edge of the cover means, said first rigidifying means for positioning behind the knee when said cover means is applied to the patient, second and third rigidifying means, each second and third rigidifying means including hook means for detachable and adjustable securement to said cover means at the loop means thereof, and means for securing said cover means about said knee, said second rigidifying means being adjustably secured to said cover means between said first rigidifying means and one cover means side edge with the hook means of the second rigidifying means interlocking with the loop means of the cover means for positioning at the inside of said knee when said cover means is applied to the patient, said third rigidifying means being adjustably secured to said cover means between said first rigidifying means and the other cover means side edge with the hook means of the third rigidifying means interlocking with the loop means of the cover means for positioning at the outside of said knee when the cover means is applied to the patient.

5. The knee immobilizer of claim 4 wherein each of said second and third rigidifying means includes an encasement part enclosing a stay component with said hook means forming a portion of the encasement part.

* * * * *